US010223833B2

(12) United States Patent
Lewis et al.

(10) Patent No.: US 10,223,833 B2
(45) Date of Patent: Mar. 5, 2019

(54) APPARATUS AND METHOD FOR AUGMENTING SIGHT

(71) Applicant: eSIGHT CORP., Kanata (CA)

(72) Inventors: Conrad W. Lewis, Kanata (CA); Daniel Mathers, Waterloo (CA); Robert Hilkes, Ottawa (CA); Rejean J. Y. B. Munger, Ottawa (CA); Roger Colbeck, Ottawa (CA)

(73) Assignee: eSight Corp., Kanata, Ontario (CA)

(*) Notice: Subject to any disclaimer, the term of this patent is extended or adjusted under 35 U.S.C. 154(b) by 0 days.

(21) Appl. No.: 15/709,984

(22) Filed: Sep. 20, 2017

(65) Prior Publication Data

US 2018/0012414 A1 Jan. 11, 2018

Related U.S. Application Data

(63) Continuation of application No. 13/947,376, filed on Jul. 22, 2013, which is a continuation of application (Continued)

(51) Int. Cl.
G06T 19/00 (2011.01)
G02B 27/01 (2006.01)
(Continued)

(52) U.S. Cl.
CPC .......... *G06T 19/006* (2013.01); *G02B 27/017* (2013.01); *G06Q 50/22* (2013.01); *G09B 21/008* (2013.01); *G02B 2027/014* (2013.01); *G02B 2027/0112* (2013.01); *G02B 2027/0118* (2013.01); *G02B 2027/0138* (2013.01)

(58) Field of Classification Search
CPC .......... G02B 27/017; G02B 2027/0112; G02B 2027/0118; G02B 2027/014; G06T 19/006; G06Q 50/22; G09B 21/008
See application file for complete search history.

(56) References Cited

U.S. PATENT DOCUMENTS 5,359,675 A * 10/1994 Siwoff ................. G02B 27/017
345/8
5,777,715 A * 7/1998 Kruegle ............... G02B 23/125
345/8
(Continued)

Primary Examiner — Yon J Couso
(74) Attorney, Agent, or Firm — Rosenberg, Klein & Lee

(57) ABSTRACT

A method of augmenting sight in an individual. The method comprises obtaining an image of a scene using a camera carried by the individual; transmitting the obtained image to a processor carried by the individual; selecting an image modification to be applied to the image by the processor; operating upon the image to create a modified image using either analog or digital imaging techniques, and displaying the modified image on a display device worn by the individual. The invention also relates to an apparatus augmenting sight in an individual. The apparatus comprises a camera, carried by the individual, for obtaining an image of a scene viewed by the individual; a display carried by the individual; an image modification input device carried by the individual; and a processor, carried by the individual. The processor modifies the image and displays the modified image on the display carried by the individual.

17 Claims, 8 Drawing Sheets

Related U.S. Application Data

No. 13/371,521, filed on Feb. 13, 2012, now Pat. No. 8,494,298, which is a continuation of application No. 12/060,964, filed on Apr. 2, 2008, now Pat. No. 8,135,227.

(60) Provisional application No. 60/921,468, filed on Apr. 2, 2007.

(51) Int. Cl.
*G06Q 50/22* (2018.01)
*G09B 21/00* (2006.01)

(56) References Cited

U.S. PATENT DOCUMENTS

| | | | | |
|---|---|---|---|---|
| 6,084,556 | A * | 7/2000 | Zwern | G09B 21/008 345/158 |
| 6,999,046 | B2 * | 2/2006 | Karstens | A61B 3/063 345/7 |
| 7,549,743 | B2 * | 6/2009 | Huxlin | A61H 5/00 351/203 |
| 8,454,166 | B2 * | 6/2013 | Fateh | A61H 5/00 351/246 |
| 2002/0101568 | A1 * | 8/2002 | Eberl | G02B 27/017 351/211 |
| 2004/0136570 | A1 * | 7/2004 | Ullman | G06T 5/004 382/114 |

* cited by examiner

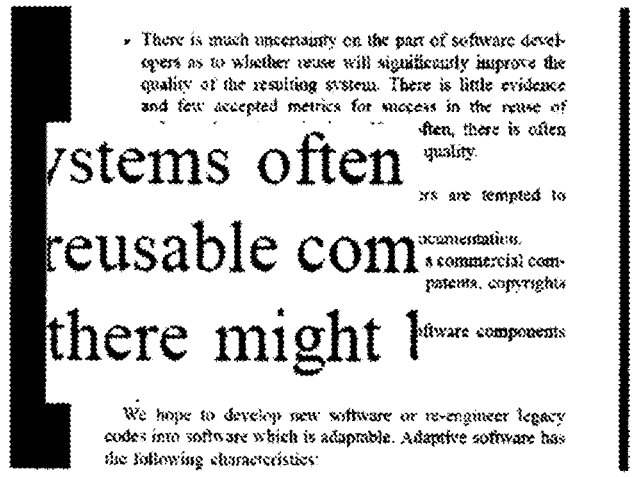

Figure 2B

- There is much uncertainty on the part of software developers as to whether reuse will significantly improve the quality of the resulting system. There is little evidence and few accepted metrics for success in the reuse of software in real applications. Very often, there is often a trade off between performance and quality.
- The learning curve could be steep.
- Highly motivated software developers are tempted to rewrite code.
- Old systems often ha documentation.
- If the reusable compo a commercial company, there might be to patents, copyrights and royalty payments.

For a comprehensive introduction to software components and reuse, see [10].

D. *Adaptive Software*

We hope to develop new software or re-engineer legacy codes into software which is adaptable. Adaptive software has the following characteristics:

- *Program for change:* Although it is hard to predict the future, objects should not make assumptions which are valid for only a short duration of time. Whenever possible, a good design should abstract some core concepts into a small number of functions and classes, and provide simple interfaces to access the functionality.

Figure 3A

- There is much uncertainty on the part of software developers as to whether reuse will significantly improve the quality of the resulting system. There is little evidence and few accepted metrics for success in the reuse of software in real applications. Very often there is often a trade
- The leave little or no dc
- Highly ed to rewrite
- Old sys
- If there (com-pany, th rights and roy
- For a comnent comes from ments and reuse, se issues related to

*D. Adaptive Software*

We hope to develop new software or re-engineer legacy codes into software which is adaptable. Adaptive software has the following characteristics:

- *Program for change:* Although it is hard to predict the future, objects should not make assumptions which are valid for only a short duration of time. Whenever possible, a good design should abstract some core concepts into a small number of functions and classes, and provide simple interfaces to access the functionality.

Figure 3D

DAT IMAGE

M2-SC1  Gradient without Suppression

M3-SC2  Gradient with Suppression

APPARATUS AND METHOD FOR AUGMENTING SIGHT

CROSS-REFERENCE TO RELATED APPLICATIONS

This application is a continuation of U.S. patent application Ser. No. 13/947,376 entitled "Apparatus and Method for Augmenting Sight" filed 22 Jul. 2013, currently pending, which itself is a continuation of U.S. patent application Ser. No. 13/371,521 entitled "Apparatus and Method for Augmenting Sight" filed 13 Feb. 2012, which issued as U.S. Pat. No. 8,494,298 on 23 Jul. 2013, which itself is a continuation of U.S. patent application Ser. No. 12/060,964 entitled "Apparatus and Method for Augmenting Sight" filed 2 Apr. 2008, which issued as U.S. Pat. No. 8,135,227 on 13 Mar. 2012, which claims priority from U.S. Provisional Patent Application 60/921,468 entitled "Apparatus and Method for Augmenting Sight" filed 2 Apr. 2007.

FIELD OF THE INVENTION

The invention relates generally to the field of vision care and more specifically to the field of augmenting sight.

BACKGROUND OF THE INVENTION

There are conditions under which even individuals with 20/20 vision need sight augmentation. Such conditions may be brought on by low light levels, low or no color differentiation between objects in the visual field, or the small size of the object viewed, to name but a few. Individuals with less than optimal vision or with other visual defects, such as retinopathies, also need augmentation to correct for their visual defects.

FIG. 1 is a schematic diagram of the eye. A portion of the retina responsible for fine detail vision is the macula. One form of visual defect is AMD, or age-related macular degeneration. In macular degeneration, which begins with the deposit of druesends in layers beneath the photoreceptors, the degenerative process affects mostly the macula and results in death of cells necessary for vision. In some patents, the result of macular degeneration is a central visual field blind-spot or scotoma. At this time there is no cure for AMD. Other diseases (such as, but not only, diabetic retinopathy, glaucoma, macular edema, optic nerve atrophy, etc.) can also result in significant losses in vision, sometimes macular, sometimes peripheral, to this region of high quality vision. Furthermore, the diseases' impact on vision is unique for each patient. What these vision losses have in common is the loss in quality of life due to the limited quality of vision.

There have been attempts to augment the quality of the perceived visual field using such items as image intensity amplifiers, or "night scopes", or mechanical or electrical image magnifiers. These devices tend to be big, bulky, limited in their application and not appropriate for non-military or paramilitary uses.

What is needed then is a general device that is capable of augmenting an image to be viewed by an individual, whatever the source of the image, be it a computer display, a television or other image source, under the command of that individual, to aid the individual in poor viewing conditions or to overcome physiological and psychological visual defects in the individual. The present invention addresses this need.

SUMMARY OF THE INVENTION

The invention, in one aspect, relates to a method of augmenting an image to be viewed by an individual. In one embodiment, the method comprises the steps of: obtaining an image of a scene viewed by the individual using an image capture device carried by the individual; transmitting the obtained image to a processor carried by the individual; selecting appropriate image modification to be applied to a region of interest in (ROI) in the image by the processor; and operating, by the processor, upon the image to create a modified image in response to the selected image modification or modifications; and displaying the modified image on a display device worn by the individual. In one embodiment, the image modification is magnification. In another embodiment, the image modification is a remapping of the image to avoid visual defects in the individual. In another embodiment, the image modification is minification, or fractional magnification. In another embodiment, the image modification overlays minified peripheral information into the central area of the field of view. In yet another embodiment, the image modification is a remapping of colors within the image. In still yet another embodiment, the image modification is edge enhancement. In another embodiment, the image modification is image intensity enhancement. In one embodiment, the image modification takes place substantially in real time. Other embodiments may include combinations of these and other functions.

In another aspect, the invention relates to an apparatus for augmenting an image viewed by an individual. In one embodiment, the apparatus comprises an image capture device carried by the individual, for obtaining an image of a scene viewed by the individual; a display carried by the individual; an image modification input device carried by the individual; and a processor carried by the individual. The processor is in communication with the image capture device, image modification input device and display. The processor modifies the image obtained by the image capture device, in response to the instructions provided by the individual using the image modification input device, and displays the modified image on the display carried by the individual.

In one embodiment, the display comprises a pair of glasses. In another embodiment, the image capture device is attached to a pair of glasses. In yet another embodiment, a second image capture device and a second display are in communication with the processor. The second image capture device provides a second image for the processor to modify and display on either the first or the second display.

In yet another aspect, the invention relates to a method for improving the visual function. In one embodiment, the method includes the steps of: determining the locations of retinal damage in an eye of the patient; obtaining an image of a scene to be viewed by the patient; and mapping the image to a display in such a way to avoid the locations of retinal damage when the display is viewed by the patient. In another embodiment, the step of obtaining the image uses an image capture device attached to the glasses of the patient. In yet another embodiment, the display replaces a lens of the glasses of the patient.

Another aspect of the invention relates to an apparatus for improving the visual acuity of a patient with a degenerative disease of the retina. In one embodiment, the apparatus includes a camera for obtaining an image of a scene to be viewed by the patient; a display; a memory storing locations of retinal damage of the eye of the patient; and a processor, in communication with the image capture device, display and memory, for mapping the image to the display in such a way as to avoid the locations of retinal damage when the display is viewed by the patient. In another embodiment, the display replaces a lens of the glasses of the patient.

DESCRIPTION OF THE DRAWINGS

The invention is pointed out with particularity in the appended claims. The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

FIG. 2b is an example of an image modified by this method;

FIG. 3a is an example of an image as viewed with a blind spot defect in the visual field;

FIG. 3d is an example of an image as viewed with a blind spot defect in the visual field but with magnification and horizontal spacing generated by a "horizontal split" algorithm;

DETAILED DESCRIPTION

Figure 1:
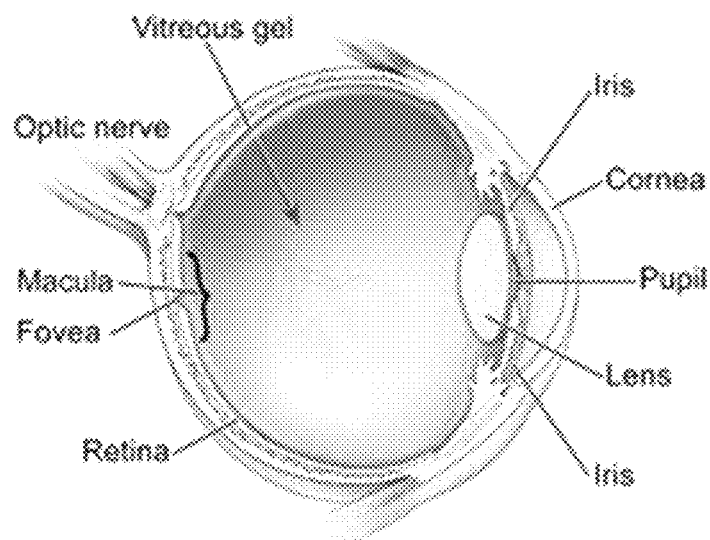
FIG. 1 is a diagram of the eye.
Figure 2:
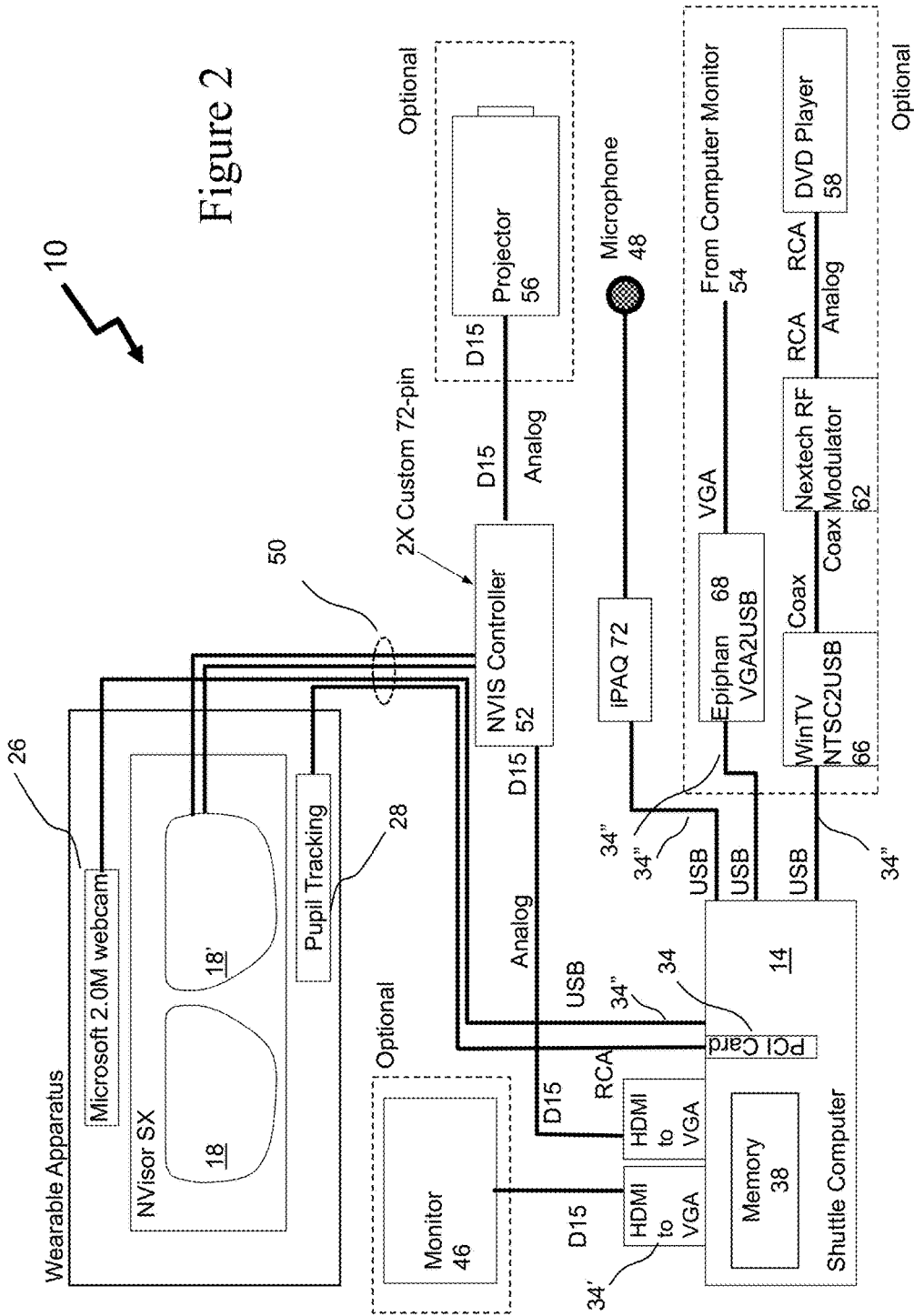
FIG. 2 is a highly schematic diagram of an embodiment of the system of the invention.

In brief overview and referring to FIG. 2, the system for augmenting sight in one embodiment includes a pair of eyeglass frames 10 or headmounted display, such as an Nvisor SX, by NVIS (Reston, Va.), and a processor 14. In one embodiment, the processor 14 is a general purpose computer, such as made by Shuttle Computer Group (City of Industry, Calif.). The eyeglass frames 10 are the typical eyeglass frames generally available and used today with transparent lenses. In this embodiment, the transparent lenses have been replaced with one or two display screens 18, 18' (generally 18). Attached to the frame are one or more image capture devices 26, such as a camera. In one embodiment, the image capture device is a Microsoft 2.0M Webcam (Redmond, Wash.). Optionally, one or more eye or pupil tracking sensors 28 and associated electronics are also attached to the frame. The electronics provide for image capture by the image capture device and transmission to the processor 14 by way of a wired or wireless link 50. The processor 14 includes one or more input output (I/O) modules 34, 34', 34" and a memory 38 in communication with each other by way of a bus as in standard computer design. The I/O modules 34, 34', 34" not only receive images from the image capture device 26, but transmit the modified images back to the eyeglass frames for display on one or both of the display screens 18, 18'. With two or more image capture devices 26, the resulting images each may be displayed on a respective display 18, 18' to provide depth perception (depending on the capture device position), or one image capture device 18 can select an region of interest (ROI) in the field of view (FOV) of the other image capture device 18' and display the region of interest within the field of view on both displays. In this way, for example, a magnified region of interest may be displayed in the larger field of view.

In more detail, in various embodiments, the displays 18, 18' in the eyeglass frames 10 include, in one embodiment, a thin film display such as a liquid crystal display. In another embodiment, the displays use Liquid Crystal on Silicon (LCOS) technology. In a further embodiment, the displays use Organic Light Emitting Diode (OLED) technology. In still a further embodiment, the displays use micro-projection technology onto a reflective (partial or 100% reflective) glass lens. In various embodiments, each display shows a different image or the same image. If the modified image is to be displayed only to one eye, only one display 18 is required. The displays in various embodiments can incorporate refractive lenses similar to traditional eyeglasses, such that the display works in concert with a person's unique optical prescription.

Similarly, the image capture device 26 in one embodiment is a charge coupled device (CCD) camera with high depth-of-field optics. In another embodiment, the image capture device is a Complimentary Metal Oxide Semiconductor (CMOS) image sensor with appropriate optics. In other various embodiments, the image capture device is any imaging device with an analog or digital signal output that can be sent to a processing unit 14 for processing. In a binocular configuration, each image capture device or camera 26 sees a slightly different image, thereby providing stereoscopic vision to the viewer. If the image is to be presented to only one eye, then only one image capture device or camera 26 is needed to record the image for that eye. Although in the embodiment shown the image capture device or camera 26 and related electronics are mounted on the eyeglass frames 22, it is contemplated that the camera 26 and electronics could also be located elsewhere on the individual's person. Also, although two cameras 26 are contemplated for binocular vision, it is possible for one camera 26 to view the image and present the same image to both displays 18. In addition, in various other embodiments the source of the image may be another camera, a television, a computer 54 or other source 58 capable of supplying an input to the processor 14.

The optional eye tracking sensor 28 is also in communication with the electronics and determines where in the visual field the individual is looking. In one embodiment, this sensor 28 operates by following the position of the pupil. Such eye tracking devices 28 are common in presently available "heads-up-displays" utilized by military pilots. Again, although an embodiment contemplated includes two tracking sensors 28, because both eyes typically track together, one tracking device may be used. In another embodiment, the eye tracking sensor uses a combination of mirrors and prisms such that the optical path for the eye tracking sensor is orthogonal to the pupil. Eye tracking is used to determine the region of interest (ROI), and to ensure that the damaged areas of a person's vision are avoided when the modified image is presented to the eye. The eye-tracking information is suitably averaged and dampened in software to minimize the sensitivity to random eye movements, blinks, etc., and to optimize the system for various usage models. For example, reading English requires specific eye tracking performance in the left to right direction different from that in the right to left direction, and different again from that in the vertical direction.

Images from the image capture device 26, eye position information from the eye tracking device 28 and images destined for the displays 18 are passed through the appropriate I/O module 34, 34', 34" (HDMI to VGA, PCI and USB respectively) of the processor 14. In the embodiment shown, the display on the NVISOR SX display unit is controlled by an nVIS controller 52 by the same manufacturer of the NVISOR SX display 18. This communication between the processor 14 and the electronics of the eyeglass frames 10 may be transmitted through a wired connection 50 or be transmitted wirelessly. Certain functions, such as magnification, may be performed in an analog manner, such as by adjusting the lens array on the camera or digitally by mathematically processing pixels.

In the embodiment shown, the processor 14 is a Shuttle computer having memory 38 and I/O modules 34, 34', and 34". The I/O modules not only communicate with the eyeglass frames 10 but also with other displays and input devices. For example, the processor 14 may be connected to a second optional monitor 46, so that a health care provider or device technician can see what the wearer is seeing. In addition, the NVIS controller 52 is capable of providing video data to a projector 56. In this way, greater numbers of individuals may see what the wearer is seeing.

Additionally, display images from a computer 54 and from a video source 58 such as a DVD may provide images for display on the display of the eyeglass frames 10. Such images may be used to help train the wearer to diagnose hardware and software failures and to help diagnose and treat the patient. In one embodiment, an input device such as a DVD player 58 provides a signal to an RF modulator 62 which then passes the RF image signal to the processor 14 through a Win TV NTSC to USB module 66. This signal enters the processor 14 through a USB connector 34". Similarly, image data from a computer monitor 54 may also be displayed on the glasses 10 by converting the signal from the monitor 54 using a VGA to USB converter (for example an Epiphan Systems converter, Ottawa, Ontario, Canada.) 68. Additionally, the user may wear a ring-like "text-camera" on his or her finger which he or she then scans over a line of text. Such devices reduce the optical complexity of the eyeglass camera 26. Finally, in this embodiment, input commands may be entered by way of a microphone 48 in communication with an iPAQ computer 66.

The processor 14 in another embodiment is a processing device having cellular telephone capabilities or a software modified cellular telephone. In this embodiment data, for example from an ophthalmologist or other health care professional 46, may be received from the cellular telephone network and verbal control instructions from the individual 48 may be input through the phone's microphone or alternatively may be keyed in through the phone's touchpad or movement sensor. In other embodiments, the processor is a specialized computer or handheld device.

Received data and control instructions are then stored in memory 38. The memory 38 includes random access memory (RAM) for data storage and program execution, and read only memory (ROM) for program storage. The microprocessor 14 accesses the data in memory and manipulates it in response to the control instructions for transmission back to the eyeglass frames 10 for display. In this way, the individual can tailor the displayed image for optimal viewing.

Figure 2A:
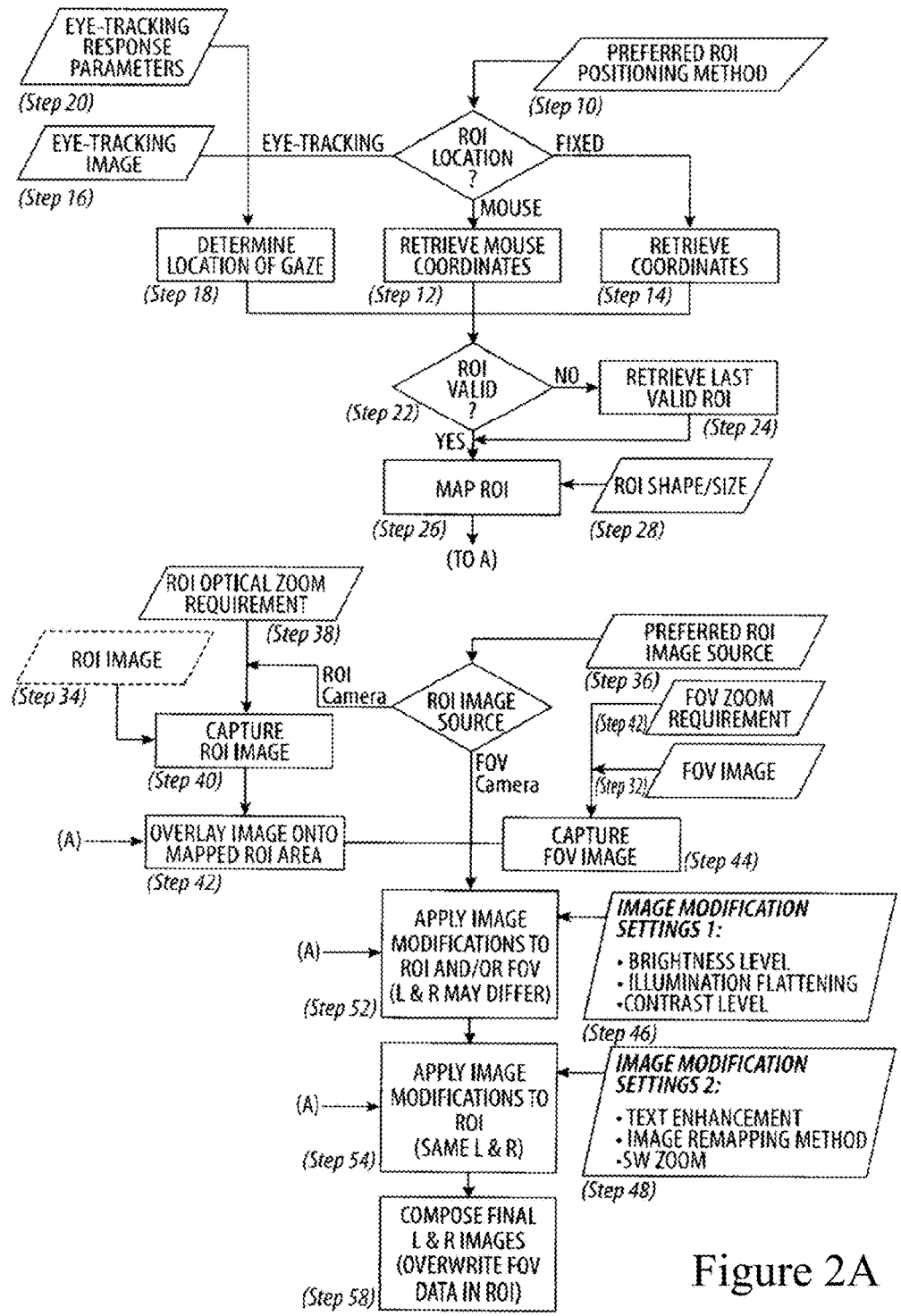
FIG. 2a is a flow diagram of an embodiment of a method, implemented by the system of FIG. 2, to modify an image.

One embodiment of the method using the system which is capable of modifying an image of the field of view is shown in FIG. 2a. The wearer begins by setting the preferred method of determining the location of the region of interest (ROI) through a keyboard or other input device (step 10). The individual may indicate their preferred location of the ROI by selecting one of a mouse input (step 12), preset coordinates (step 14) or eye-tracking imaging (step 16).

If an eye tracking sensor 28 is used, the individual need only move their eye to determine the region of interest (step 18). Some mathematical parameters are applied to determine the sensitivity of the eye tracking algorithm in the X and Y directions (step 20) to minimize the effect of involuntary eye movement on the choice of region of interest.

From this information, the center of the region of interest (ROI) is determined. If the region of interest (ROI) is not within the viewing area (step 22), the region of interest is set to the last valid region of interest (step 24). The complete region of interest (ROI) is then determined, or "mapped" such that it is centered on the coordinates determined (step 26). The size and shape of the ROI is determined through user inputs (step 28).

The visual information in the region of interest (ROI) may be input from either the field of view (FOV) image (step 32), or from a separate region of interest image source (step 34), as determined by user input (step 36). If the ROI image is to come from a separate source (step 36), then the user can input an optical zoom requirement (step 38) for this image. The ROI image is then captured (step 40) and overlaid or mapped, onto the ROI area (step 42).

The individual sets the zoom requirement (step 44) for the field of view (FOV) image. The zoom function is a combination of both optical zoom done in the FOV camera using lenses, and digital zoom performed in software. The FOV image is then captured. (step 44).

The image is then modified (steps 24 and 25) as further required by the user input values (steps 46 48, and 54). Note that some modifications are applied to the left and right displays, or left and right eyes, differently (step 52), while others are applied to the left and right displays equally (step 54). Any of the image modifications may be applied to either the region of interest (ROI) or the entire field of view (FOV), or both. The final modified images are then presented to the displays (step 58). FIG. 2b depicts what the displayed magnified text would look like.

Figures 3B, 3C:
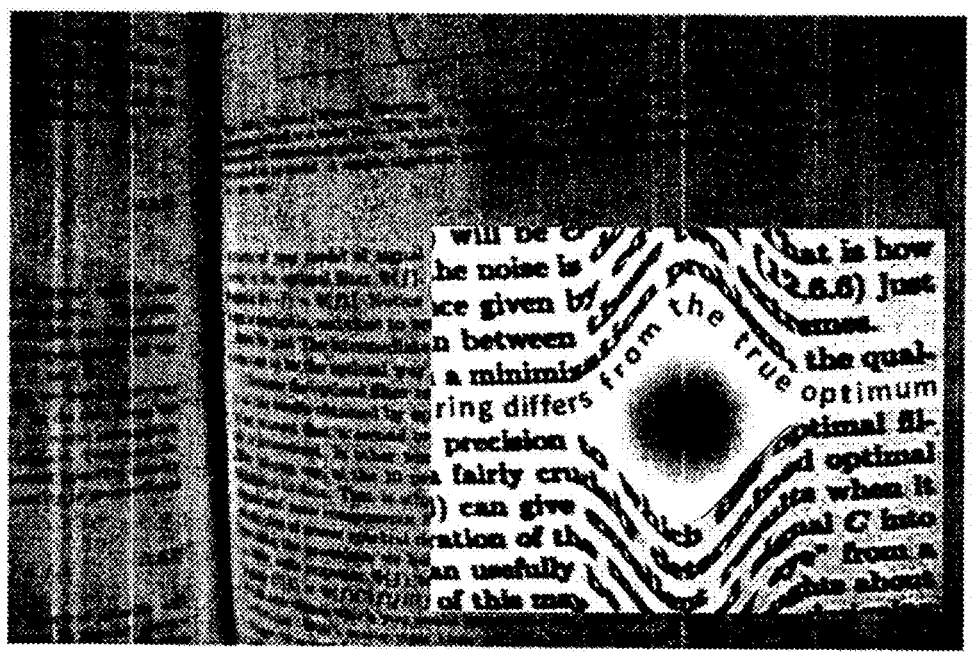
FIG. 3b is an example of an image as viewed with a blind spot defect in the visual field but with the image magnified.
FIG. 3c is an example of an image as viewed with a blind spot defect in the visual field but with magnification and deformation generated by a "pushout" algorithm.

Referring also to FIGS. 3, the system can also be used to correct vision defects in the eyes of the individual. In this example, an individual has a defect in his or her visual field that causes a perceived image defect as shown in FIG. 3a. As a first step, an ophthalmologist performs an eye examination on the individual, mapping the areas of the eye which are not functioning properly. This information is downloaded to the memory 38 of the processor 14 through the I/O module 34. The processor can then map the image to avoid the defect as is shown in FIGS. 3b, 3c and 3d. The end result is that the remapped image removes loss of information (previously hidden behind the defect) caused by the defect as shown in FIGS. 3b and 3c. In FIG. 3b the text is magnified about the defect region, while in FIGS. 3c and 3d the text is remapped to be spaced about the defect. Thus, with training the individual is capable of seeing a full image substantially free of distortion. The individual may perform many types of image modification by entering data through the keypad of the device or by speaking instructions through the microphone of the device.

The device is designed to help anyone having to deal with visual challenges which cannot be addressed by simple optical means (glasses, contact lenses, etc). Visual challenges can be due to either less than optimal performance of the visual system or environmental conditions. The visual system is a complex structure which combines an optical imaging system (the front end of the eye), a network of sensors (the photoreceptors) positioned at or near the focal plane of the imaging system and a complex neural network (and its supporting infrastructure of cells) for processing the information from the sensors into a visual signal. A problem in either the optical, sensing or neural component of vision will result in less than optimal vision. The resulting visual problems can manifest themselves in many ways including, but not limited to, a reduced ability to see fine details; a reduced sensitivity to contrast; a reduced ability to extract color information; a loss in peripheral field of view; a loss of central field of view; and an increased sensitivity to brightness.

These various types of vision loss can be the result of trauma to the eye or disease of the eye. Most of these diseases affect the back of the eye (retina) where light sensing and some signal processing occurs. Glaucoma, diabetic retinopathy, age-related macular degeneration (AMD), and retinitis pigmentosa are some of the more common causes of vision loss in the developed world. The resulting visual problems and their extent vary from almost no noticeable effect to complete blindness and are unique to each patient.

The invention is not disease specific, and is able to address the major diseases discussed above as well as most other retinal conditions (such as, but not limited to retinopathies, optic disc neuropathies, Stargardt's disease, retinal dystrophies, most variations of macular/foveal edema, etc.) short of profound blindness, by dramatically improving the wearer's visual experience and ability to function beyond that which is possible without the invention.

The proposed solution can also be helpful, if likely to a lesser extent, to patients with degraded optical properties including optical errors in the cornea (front element of the eye), the crystalline lens (lens inside the eye) and any issues with the liquid contained within the eye (scattering sites, opacification, etc.).

Finally, the invention can also help some people with visual problems due to higher level processing errors in the brain such as, but not limited to, compensating for missing portions of their field of view, problems with tracking, problems that are helped by improving mental focus and removing peripheral distractions (such as dyslexia), etc.

Outside of visual problems, there are many environmental conditions that can lead to poor visual information transfer. As an example, trying to look at someone's face while they stand in front of a window on a bright sunny day, looking at a baseball game where part of the field is in sunlight and another in shadows, poor quality illumination (lots of blue for example). The device can certainly help most of these people reduce the impact of the environmental condition on their visual performance. These conditions can occur during work or leisure activities, for example facing the sun up on a telephone pole while performing a repair, walking the dog, attending a sports event, etc.

Finally, the device can enhance the amount of information available to normally sighted people. It can overlay multiple sources of information on a same field of view. This can be used in professional applications, for example, to call up stock figures or inform a wearer of incoming email overlaid upon a real-world image while walking down the street; to call up an electrical wiring diagram overlaid with a magnified image of broken down electric circuit to effect a repair. These images will not only be overlaid, but can be manipulated to optimize information delivery and minimize disturbance from natural visual experience. Also, the invention enables hands-free access to this information, which is critically important in some applications.

To correct for these conditions the user can issue instructions that cause the processor 14 to perform operations on the image including but not limited to:

1. Magnify field of view (FOV) or ROI—this function permits the field of view to be decreased and the resolution increased up to the resolution of the camera and the resolution of the display.

2. Minification: Reducing the FOV to a smaller size to account for conditions which manifest themselves as "tunnel vision". This is equivalent to fractional magnification.

3. Enhance contrast in entire FOV or only ROI—this function permits contrast contained naturally in the image to be modified so as to enhance the difference between various levels of contrast to improve the detection of information in the image.

4. Enhance edges in entire FOV or only in ROI—this function permits the edge of an object in the field of view to be detected and enhanced (for example, but not limited to, adding a black band) to improve the ability of the patient to perceive the edges of different features of the image.

5. Change to grey scale in entire FOV or only in ROI—this function permits the image to be converted to a grey scale from a color scale.

6. Threshold grey scale in entire FOV or only in ROI—this function permits all the colors and intensities of the image to be mapped into either black or white.

7. Remap colors in entire FOV or only in ROI—this function remaps the colors in the original image into another range of colors, thereby permitting color blindness or deficiency to be ameliorated.

8. Remap image based on the user's blind spot in ROI—this function allows the individual to remap the image to avoid the blind spots caused by diseased regions of the eye, such as in macular degeneration or Stargardt's disease. Various algorithms relocate pixels from behind a blind spot to areas near the periphery of the blind spot according to a mathematical spatial distribution model.

9. Relocation and Enhancement of Text: This technique is a specific implementation of "Spatial Remapping" above, where text is moved out from behind a blind spot. The technique includes application sensitive techniques such as only splitting the image on the blank lines between text lines, serif removal, text edge smoothing, text enhancement through color and contrast improvement, optical character recognition (OCR), etc.

10. Brightness adjustment of field of view or region of interest: Individual pixels can be modified to increase or decrease their brightness either globally or according to a mathematically defined spatial distribution.

11. Brightness flattening of field of view or region of interest: The variation in brightness across an image can be reduced, such that "hotspots" or washed out regions are darkened, and dark areas are brightened.

12. Image Superimpositioning: This is a technique where peripheral information is overlaid into a central area of the FOV, in order to provide contextual data to people with lost peripheral visual performance.

14. Color Identification: The invention can identify (via screen text) the dominant color or the statistical red-green-blue (RGB) content for a specific portion of the image, as identified for example by "cross-hairs."

15. Black/White Conversion and Inversion of field of view or region of interest: Color or grayscale images can be reduced to B/W or inverted B/W (W/B).

By using fast processors it is possible to make these modifications in substantially real time. This allows a visually impaired individual to function substantially as if there were no visual defect. With a fast enough computer, these enhancements may be applied and removed sequentially to an image, that is the image toggled between the actual image or the image as modified, by the user so that the user sees the original image and the enhanced image as a repeating toggled sequence. This provides the user with a clearer sense about what aspects of the presented image are "real" and which are "enhancements".

Further certain enhancements can be applied and removed from the image automatically. For example, an edge enhancement modification can be applied and removed sequentially and repetitively such that the user sees an edge enhanced image and then the unmodified image.

Many algorithms can be used to achieve these purposes. For example, one embodiment of an edge finding algorithm detects edges using a gradient operator. To avoid noise due to small natural variations in intensity of the image, the gradient operator is applied to a low pass digitally filtered version of the image. If the digital filter is a Gaussian, then the gradient of the filtered image is simply the convolution of the image with the gradient of the filter; the Canny Gradient Operator. This technique has two major advantages. Firstly, this technique avoids the issue of having to calculate a finite derivative of the natural image. Although the derivative of the Gaussian function is known analytically, the derivative of the natural image is mathematically ill-posed. Second, this technique permits both the filtering and derivative operations to) be performed simultaneously in Fourier space. This is represented by:

$$\nabla f_\sigma(x, y) = (f * \nabla g_\sigma)(x, y)$$

where f and $f_\sigma$ are the unfiltered and filtered images respectively and $g_\sigma$ is the Gaussian filter. The amount of filtering applied will be controlled by the Gaussian width ($\sigma$). One embodiment of the implementation separates the gradient operator into its two Cartesian coordinates, so that in its final form the gradient is:

$$\nabla_x f_\sigma(x, y) = \left(f * \frac{\partial g_\sigma}{\partial x}\right)(x, y),$$

$$\nabla_y f_\sigma(x, y) = \left(f * \frac{\partial g_\sigma}{\partial y}\right)(x, y),$$

$$M_\sigma(x, y) = \sqrt{(\nabla_x f_\sigma(x, y))^2 + (\nabla_y f_\sigma(x, y))^2},$$

$$\Theta_\sigma(x, y) = atan\left(\frac{\nabla_y f_\sigma(x, y)}{\nabla_x f_\sigma(x, y)}\right)$$

Figure 4A:
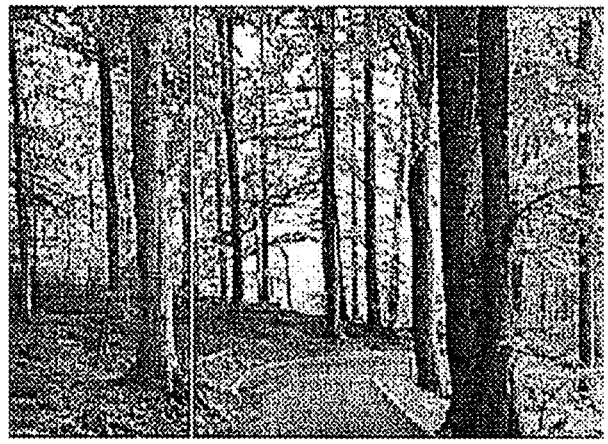
FIG. 4 (a-c) respectively depict an image, the image with the gradient applied and the image with the gradient applied with suppression.
Figure 4B:
Figure 4C:
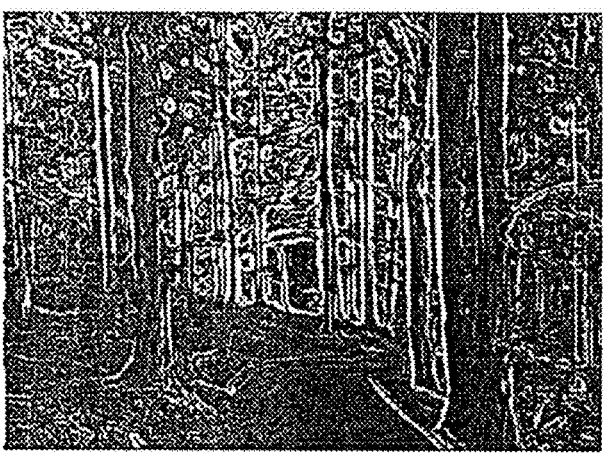

This generates an amplitude term (M) which is the vector sum of the two components and a direction component ($\Theta$). The result of this filtering is a gradient map which does not show edges specifically. The gradient image is then processed to identify edges by first using a bi-linear interpolation around each point in the image to identify the points which are local maxima. Once identified, only the local maxima are retained and all other points are ignored. Then the direction of the gradient is used to identify adjacent points which are connected, because the gradient will be similar for adjacent points if they are part of the same edge. Other outliers in the gradient are rejected. Finally, a thresholding algorithm is applied which retains all gradient points having a value in the upper percentile (in one embodiment, threshold 1, the $90^{th}$) and rejects all weak gradients having a value in the lower percentile (in one embodiment, threshold 2, the lowest $20^{th}$). Anything in between the two thresholds is rejected if it has no strong companion near it, and kept if its neighborhood indicates an edge. All retained gradient points are then binarised to 1, all others to 0, creating the outline of edges in the image. FIG. 4a depicts an image in its natural state. FIG. 4b depicts the image of FIG. 4a with a gradient applied, and FIG. 4c depicts the image of FIG. 4b with suppression of the underlying image.

Similarly, an example of a color remapping algorithm is next described. Normally sighted people depend on both brightness and color differences (luminance and color contrast) to identify features in their visual field. Abnormal color vision will often result in the inability to distinguish between colors; a reduced capacity to use color contrast to extract information. Color confusion is usually asymmetric, so that color confusion occurs along the Red-Green or Yellow-Blue color axis. This means that by remapping colors in the field of view which are confusing to an observer to color in the spectrum which offer better contrast, it is possible for the user to recover the information content of the field of view.

The algorithm described below is intended to remap the color contained in the field of view to allow the user to extract maximum content information. The color content of the processed field of view will not be true to the real world thus actual color information will not always be natural, but the color contrast will be enhanced for the observer so that there will be little or no confusion due to reduced color contrast between the objects in the field of view. This will allow the observer to identify a maximum number of details and maximize information extraction.

Figure 5:
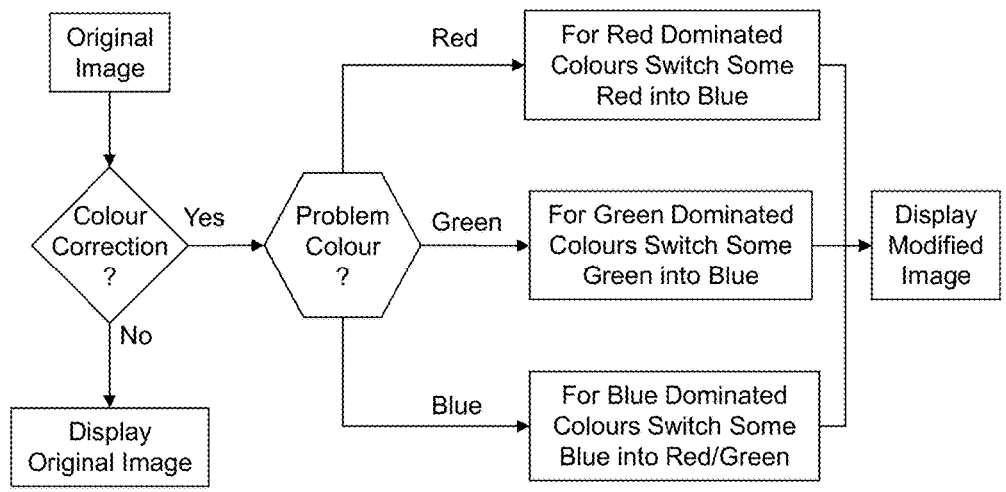
FIG. 5 is a flow diagram of an embodiment of a color-mapping algorithm.

The algorithm is illustrated in FIG. 5. If a color perception defect is identified in a patient, then the image is modified by shifting some of the color in the defective color channel (Red-Green or Blue-Yellow) in the other color channel. Two parameters are typically required. The first is to identify which colors in the image must be modified, and the second is to determine the amplitude of the color shift necessary to move the affected colors to the unaffected color channel.

First, the colors to be modified are selected by the amount of the affected primary color (Red, Green or Blue) in the image. For example, if the color defect is the inability to detect color contrast in the red/green channel, then either the reds or greens are shifted to the blue channel; whichever gives the observer the best contrast. Given that White will contain 33% of each Red, Blue and Green primary color, then the threshold for shifting a given primary color should be >33%. The threshold will be both observer and image dependent and will need to be adjustable. The amount of remapping to the better color channel will also be observer dependent as well as image dependent and thus it too will also need to be adjustable.

For each point in the image, where R, G and B represents the intensity of each primary color, the algorithm proceeds as follows:

First, the RGB values are measured, and the brightness (T) (T=R+G+B) and the normalized color values (r,g,b) (r=R/T, g=G/T, and b=B/T) calculated. Next, for each point in the image where the color contains more than the threshold amount of the problematic primary color, a percentage, shf, of the problem primary is shifted into another primary color.

For example, if (r) is the normalized value of the problematic color then:

If r>0.4 then red the primary color is more than 40% of the color of the image and hence above the threshold.

r(n)=(1−shf (r)), where r is the normalized value of the problematic color, and r(n) is the new normalized value for the shifted red primary color. Similarly, b(n)=b+shf *r where b(n) is the new normalized value for blue primary. Finally, g(n)=g which means the normalized primary color green (g) is unmodified.

One skilled in the art would recognize that if red is not the problematic color, then similar shifts are possible for the other primary colors. Thus, if the problem primary color is green (g) then the algorithm will shift some of the primary green color (g) into blue. Similarly, if the primary color blue is the problem, then the algorithm will shift blue into red.

Figures 6A, 6B, 6C:
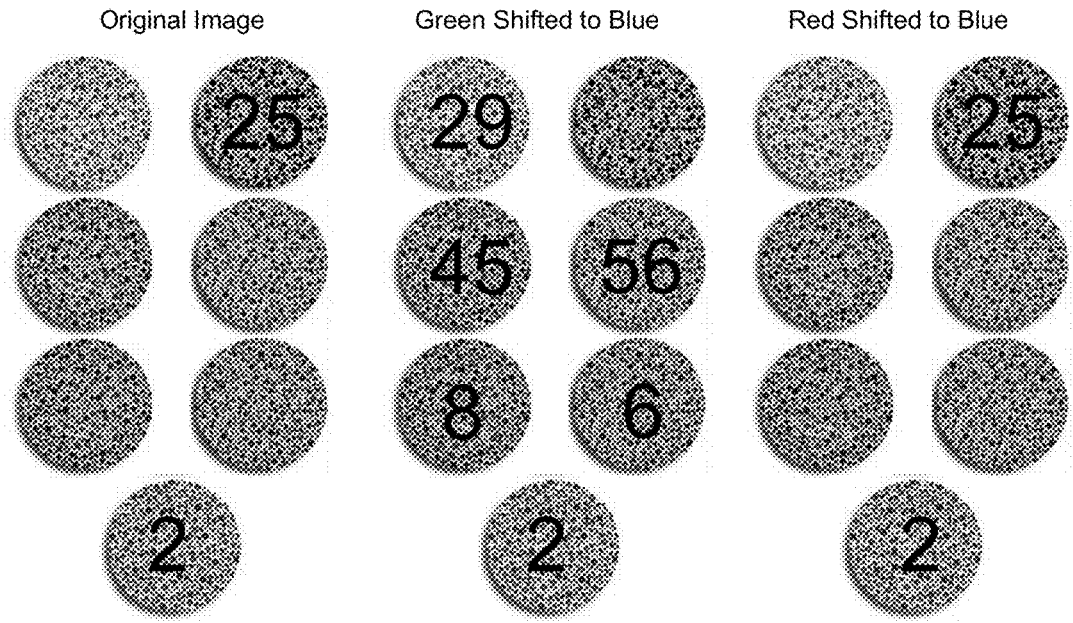
FIG. 6 (a-c) depicts a grayscale rendering of the results of mapping colors as would be seen by someone with red-green color blindness.

The new RGB coordinates of the point being examined is then the new normalized shifted color times the brightness T . Thus Rn=rn* T, Gn=gn* T and Bn=bn* T. The results of this algorithm are shown in FIGS. 6a-c.

An embodiment of the algorithm for automatic brightness and contrast enhancement transforms the image based on the intensity (signal) histogram distribution for the whole image. This technique is usually referred to as brightness/contrast equalization. An intensity distribution (number of pixels at each intensity levels), $D_A$, from the original image (A) is remapped into a new image (B) with distribution, $D_B$, with the constraints that the remapping result be single valued (each intensity level in $D_A$ can only transform to a single intensity level in $D_B$) and that the transform be reversible or monotonic.

These constraints are embodied in the equations:

$$D_B = f(D_A)$$

and $$D_A = f^{-1}(D_B)$$

Many different transforms can be used that meet these constraints. One embodiment is the algorithm discussed below. This algorithm is a simple and effective approach that is widely used in the image processing world.

This embodiment of the algorithm adds additional constraints to the determining the mapping function f ($D_A$). In one embodiment, an additional requirement is that the energy contained within a small region ($dD_A$) of the distribution $D_A$ must equal the energy to the corresponding region $dD_B$ of the distribution $D_B$ . That is:

$$h_A * dD_A = h_B * dD_B$$

where h is the number of pixels at a predetermined intensity level, (x). If the values of h are rescaled by dividing the value by the total number of pixels then the values of h can be expressed as probability distributions $p_A$ and $p_B$. Furthermore, because the intensity distribution is being stretched from the original image (0 to a maximum intensity, $D_M$) and because the area under the two probability distributions must be equal as described above, then the derivative of the transfer function df=df(x)/dx, can be set to a constant equal to $D_M$ . The transform function is then rewritten in terms of the probability distribution $p_A$ and $D_M$:

$$f(D_A) = D_M \int p_a(u) du = D_M * F_A(D_A)$$

where $F_A$ ($D_A$) is the cumulative distribution function for the original image. The implementation then becomes:

First, obtain an intensity distribution function for the original image with the same number of bins available as there are available grey levels for the display mode (that is, 8 bits gives you 256 potential bins.)

Next, normalize the distribution function by dividing it by the number of pixels to convert the distribution function to a probability function.

Third, find the largest gray level with a non zero value in the original image and set this to $D_M$.

Next create a cumulative distribution function: For example bin 0 is the number of pixels of brightness=0; bin 1 is sum of the number of pixels in bin 0 and 1; bin 2 is sum of pixels in bins 0,1,2; and so on.

Fifth, for each pixel, obtain the intensity, I(c, r) where c and r are the column and row indices, and find the cumulative probability for that intensity I(c,r); a value between 0 and 1.

Then multiply this value by $D_M$. This is the new value of the intensity for that pixel, after equalization.

Finally, to obtain stretching as well, multiply the new intensity value by the ratio of the maximum possible for display divided by $D_M$. This step ensures the maximum contrast. FIG. 6 shows a grey-scale image of a color blindness test image. FIGS. 6b and 6d depicts grey-scale images of the color blindness test image with the green shift to blue and red shifted to blue, respectively. Thus a person with red-green color blindness would be able to easily see portions of the image which would normally appear hidden.

A patient may use any function which addresses his or her visual defects by entering the requested function using the keypad. However, the parameters which the system used to correct for the defects may need to change over time. This is because typically, over time, the patient's visual preferences may evolve; or the visual defect may worsen due to the aging process, due to an accident, or disease. Further, a patient may simply prefer to change the configuration settings based on the current task they are performing, and as such may have different preferences for different tasks. Thus a user, using the control features for the display system, can adjust the settings of the optical display, allowing the user to make minor changes to his or her prescription.

When a user requires a minor change to his or her vision system settings, he or she can either go to a vision care professional, who will change the system settings, or change the settings themselves. For example, the user is able to configure a 'recipe' of image modification software algorithms to correct or enhance his or her vision in a simple, time-efficient way for a defined set of visual tasks such as watching TV, reading, playing bridge, needlepoint, etc. without the assistance of a specially trained clinician.

For major changes to the system settings, professional ophthalmic oversight may still be required. For example, the ability for a clinician to synthesize, review, modify and, if deemed appropriate, approve a user-selected image enhancement 'recipe' as above, may be required for regulated activities such as driving. The software 'recipe' would not become operational in the system, which is identified by a unique software serial number, unless and until activated by the clinician. Typically, the clinician is also identified by a unique secure government identification number provided to those clinicians authorized to approve visual aids for driving. The clinician may interact with the system directly or may remotely connect to the system. Upon clinician approval of the prescription, the clinician would then receive compensation for services. The compensation is provided by way of funds transfer from one or both of the system manufacturer, distributors or dealers and the user or his or her insurance company. The funds transfer in one embodiment is done electronically.

For example, in one embodiment, the user would enter the changes required to their settings to a settings application running on the system. The requested changes would then be indicated to the user's clinician or eye doctor by way of the settings application, allowing the new prescription to be downloaded by the optometrist or ophthalmologist. The optometrist or ophthalmologist's office system would first be paid for services rendered, by system supplier directly for initially selling the system. All fees for 'Optometric oversight' functions or adjustments would be paid directly by the insurance company or individual patient, to the eye care professional or clinician. The system adjustments could also be used to make changes to the user's prescription such that a 'configurable low vision aid' version of the system which incorporates multi-diopter lens characteristics could be used instead of refractive lenses.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What is claimed is:

1. A method of improving the visual function of a user comprising the steps of:
    storing within a non-volatile non-transitory memory associated with an electronic processor of a first electronic device first data relating to a determined vision loss relating to degradation in a predetermined portion of a visual field of view of the user;
    configuring within the non-volatile non-transitory memory a plurality of sets of second data; each set of second data relating to configuring a mode of operation of a plurality of modes of operation is established in dependence upon the first data and relates to a predetermined subset of a plurality of image processing algorithms applied by the electronic processor;
    obtaining image data from a second electronic device;
    modifying a predetermined portion of the obtained image data with the electronic processor to generate modified image data established in dependence upon applying the predetermined subset of the plurality of image processing algorithms associated with a selected mode of operation of the plurality of modes of operation to the predetermined portion of the obtained image data, the predetermined portion of the obtained image data relating to the predetermined portion of the visual field of view of the user;
    generating combined image data by digitally replacing a portion of data relating to the visual field of view of the user with the modified predetermined portion of the obtained image data; and
    projecting the combined image data onto the user's retina via a display forming part of a head mounted device coupled to the first electronic device; wherein
    the selected mode of operation is established by the electronic processor either:
        by receiving input data established by the user via an input interface of a portable electronic device coupled to the first electronic device, the input data relating to the selection by the user of a mode of operation of the plurality of modes of operation; or
        in dependence upon the visual field of view of the user;
    user generated adjustments to at least one of configure and revise the mode of operation of a plurality of modes of operation up to a predetermined level of change are employed by the first electronic device without professional oversight; and
    above the predetermined level of change a professional ophthalmic clinician is required to approve the user adjustments.

2. The method of claim 1, wherein
    the vision loss relates to at least one of a higher level processing error in the user's brain.

3. The method according to claim 1, wherein
    the portable electronic device is coupled to the first electronic device by at least one of a wired interface and wireless interface; and
    the input interface of the portable electronic device is at least one of a microphone, a touchpad, a keypad, and a motion sensor.

4. The method according to claim 1, wherein
    the second electronic device is at least one of a digital image acquisition device, a source of video data being displayed upon another display within the field of view of the user, and a third electronic device associated with the user.

5. The method according to claim 1, wherein
    modifying a predetermined portion of the image data comprises at least one of enhancing edges of objects within the predetermined portion of the image data, modifying the predetermined portion of the image data spectrally, and modifying the predetermined portion of the image data spatially.

6. The method according to claim 1, wherein
    the predetermined portion of the obtained image data to be modified is determined in dependence upon data acquired tracking the user's eye movement and the first data.

7. The method according to claim 1, wherein
    the head mounted device further comprises a corrective lens; and
    the corrective lens relates to another vision loss relating to a degradation in another predetermined portion of the visual field of view of the user other than the determined vision loss relating to the degradation in the predetermined portion of the visual field of view of the user.

8. The method according to claim 1, wherein
    modifying the predetermined portion of the image data with an electronic processor to generate modified image data in dependence upon the established mode of operation of the plurality of modes of operation relates to increasing a visual contrast of the predetermined portion of the image data within the predetermined portion of the visual field of view of the user; wherein
    the increased visual contrast within the predetermined portion of the visual field of view of the user comprises a first portion based upon applying a first image modification to the visual field of view and a second portion based upon applying a second image modification to the predetermined portion of the obtained image data.

9. The method according to claim 1, wherein
    the characteristic of the vision loss of the user relates to at least one of:
        an element the user's optical imaging system selected from the group comprising cornea, pupil, lens, iris, and vitreous gel; and
        a neural component of the user's vision.

10. The method according to claim 1, wherein
    the first data relating to the determined vision loss stored within the non-volatile non-transitory memory is acquired by the first electronic device via at least one of a wireless interface and a wired interface; and the first data is generated by at least one of an ophthalmologist and a healthcare professional.

11. The method according to claim 1, wherein
the characteristic of the vision loss of the user relates to either an environmental condition and a higher level processing error; wherein
the higher level processing error is selected from the group comprising:
compensating for missing portions of the user's field of view;
correcting a problem with the user's eye tracking;
improving mental focus; and
removing peripheral distractions.

12. The method according to claim 1, further comprising alternately projecting to the user the visual field of view and the combined image data.

13. The method according to claim 1, wherein
each mode of operation of the plurality of modes of operation relates to a different task performed by the user; and
the predetermined subset of a plurality of image processing algorithms associated with each mode of operation of the plurality of modes of operation is established by the user.

14. The method according to claim 1, wherein
the data relating to the visual field of view of the user prior to being combined with the modified predetermined portion of the image data is modified in dependence upon a second vision loss relating to a general degradation in the user's visual field of view.

15. The method according to claim 1, wherein
generating the combined image data by digitally replacing a portion of data relating to the visual field of view of the user with the modified predetermined portion of the obtained image data comprises manipulating the obtained image data from the second electronic device in order to enhance delivery of the information to the user and reduce disturbance of the modified predetermined portion of the obtained image data to the user's field of view.

16. A method of improving the visual function of a user comprising the steps of:
storing within a non-volatile non-transitory memory associated with an electronic processor of a first electronic device first data relating to a determined vision loss relating to degradation in a predetermined portion of a visual field of view of the user;
configuring within the non-volatile non-transitory memory a plurality of sets of second data; each set of second data relating to configuring a mode of operation of a plurality of modes of operation is established in dependence upon the first data and relates to a predetermined subset of a plurality of image processing algorithms applied by the electronic processor;
obtaining image data from a second electronic device;
modifying a predetermined portion of the obtained image data with the electronic processor to generate modified image data established in dependence upon applying the predetermined subset of the plurality of image processing algorithms associated with a selected mode of operation of the plurality of modes of operation to the predetermined portion of the obtained image data, the predetermined portion of the obtained image data relating to the predetermined portion of the visual field of view of the user;
generating combined image data by digitally replacing a portion of data relating to the visual field of view of the user with the modified predetermined portion of the obtained image data; and
projecting the combined image data onto the user's retina via a display forming part of a head mounted device coupled to the first electronic device; wherein
the selected mode of operation is established by the electronic processor either:
by receiving input data established by the user via an input interface of a portable electronic device coupled to the first electronic device, the input data relating to the selection by the user of a mode of operation of the plurality of modes of operation; or
in dependence upon the visual field of view of the user; and
the predetermined subset of a plurality of image processing algorithms associated with each mode of operation of the plurality of modes of operation is established by the user; and
at least one of:
user generated adjustments to at least one of configure and revise the mode of operation of a plurality of modes of operation above a predetermined level require approval of a professional ophthalmic clinician and the at least one of the configuration and revision of the mode of operation of a plurality of modes of operation cannot be employed by the first electronic device until approved; and
user generated adjustments to at least one of configure and revise the mode of operation of a plurality of modes of operation up to a predetermined level of change are employed by the first electronic device without professional oversight and above the predetermined level of change a professional ophthalmic clinician is required to approve the user adjustments.

17. A method of improving the visual function of a user comprising the steps of:
storing within a non-volatile non-transitory memory associated with an electronic processor of a first electronic device first data relating to a determined vision loss relating to degradation in a predetermined portion of a visual field of view of the user;
configuring within the non-volatile non-transitory memory a plurality of sets of second data; each set of second data relating to configuring a mode of operation of a plurality of modes of operation is established in dependence upon the first data and relates to a predetermined subset of a plurality of image processing algorithms applied by the electronic processor;
obtaining image data from a second electronic device;
modifying a predetermined portion of the obtained image data with the electronic processor to generate modified image data established in dependence upon applying the predetermined subset of the plurality of image processing algorithms associated with a selected mode of operation of the plurality of modes of operation to the predetermined portion of the obtained image data, the predetermined portion of the obtained image data relating to the predetermined portion of the visual field of view of the user;
generating combined image data by digitally replacing a portion of data relating to the visual field of view of the user with the modified predetermined portion of the obtained image data; and projecting the combined image data onto the user's retina via a display forming part of a head mounted device coupled to the first electronic device; wherein the selected mode of operation is established by the electronic processor either:
   by receiving input data established by the user via an input interface of a portable electronic device coupled to the first electronic device, the input data relating to the selection by the user of a mode of operation of the plurality of modes of operation; or
   in dependence upon the visual field of view of the user;

user generated adjustments to at least one of configure and revise the mode of operation of a plurality of modes of operation above a predetermined level require approval of a professional ophthalmic clinician; and the at least one of the configuration and revision of the mode of operation of a plurality of modes of operation cannot be employed by the first electronic device until approved.

\* \* \* \* \*